(12) United States Patent
Sleiman et al.

(10) Patent No.: US 9,856,383 B2
(45) Date of Patent: Jan. 2, 2018

(54) MIXTURE AND METHOD FOR SIMULATING SOILING AND WEATHERING OF SURFACES

(71) Applicant: The Regents of the University of California, Oakland, CA (US)

(72) Inventors: Mohamad Sleiman, Berkeley, CA (US); Thomas Kirchstetter, Oakland, CA (US); Hugo Destaillats, Scottsdale, AZ (US); Ronnen Levinson, Berkeley, CA (US); Paul Berdahl, Walnut Creek, CA (US); Hashem Akbari, Lafayette, CA (US)

(73) Assignee: The Regents of the University of California, Oakland, CA (US)

( * ) Notice: Subject to any disclaimer, the term of this patent is extended or adjusted under 35 U.S.C. 154(b) by 569 days.

(21) Appl. No.: 13/827,772

(22) Filed: Mar. 14, 2013

(65) Prior Publication Data
US 2013/0287966 A1 Oct. 31, 2013

Related U.S. Application Data

(60) Provisional application No. 61/638,949, filed on Apr. 26, 2012.

(51) Int. Cl.
*B05D 3/06* (2006.01)
*C09D 7/12* (2006.01)
*G01N 17/00* (2006.01)

(52) U.S. Cl.
CPC ........... *C09D 7/1216* (2013.01); *B05D 3/062* (2013.01); *B05D 3/065* (2013.01); *C09D 7/1233* (2013.01); *G01N 17/00* (2013.01)

(58) Field of Classification Search
CPC ................................. B05D 3/062; B05D 3/065
See application file for complete search history.

(56) References Cited

U.S. PATENT DOCUMENTS

2009/0324843 A1* 12/2009 Wegner .................. B05D 7/534
427/514
2013/0048572 A1* 2/2013 Hawks ........................ 210/747.2

OTHER PUBLICATIONS

Berdahl et al, Weathering of roofing materials—An overview, 2008, Construction and Building Materials, 22, p. 423-433.*
Terrenzio, Natural vs artificial aging: use of diffusion theory to model asphalt and fiberglass reinforced shingle performance, Sep. 1999, Proceedings of the Fourth International Symposium of Roofing Technology, p. 66-74.*
Gardenes Van Den Eynde, Passivation techniques to prevent corrosion of iorn sulphides in roofing slates, Corrosiion Science, 2009, vol. 51, p. 2387-2392.*

(Continued)

*Primary Examiner* — Dah-Wei D Yuan
*Assistant Examiner* — Nga Leung V Law

(57) ABSTRACT

This disclosure provides systems, methods, and apparatus related to simulated soiling and weathering of materials. In one aspect, a soiling mixture may include an aqueous suspension of various amounts of salt, soot, dust, and humic acid. In another aspect, a method may include weathering a sample of material in a first exposure of the sample to ultraviolet light, water vapor, and elevated temperatures, depositing a soiling mixture on the sample, and weathering the sample in a second exposure of the sample to ultraviolet light, water vapor, and elevated temperatures.

20 Claims, 19 Drawing Sheets

(56) References Cited

OTHER PUBLICATIONS

Cheng, Understanding the long term effects of environmental exposure on roof reflectance in California, Construction and Building Materials, 2012, vol. 26, p. 516-526.*

Mohamad Sleiman, et al., "Accelerated aging method to mimic changes in solar reflectance of roofing materials," presented at the International Roof Coatings Conference, Roof Coatings Manufacturers Association, Baltimore, MD, Jul. 18, 2012.

Hugo Destaillats, "Accelerated aging of roofing surfaces," presented at the Building Technologies Office Program Review, Building Technologies Office, Washington, D.C., Apr. 4, 2013.

Mohamad Sleiman, et al., "Development of an Accelerated Soiling Method that Mimics Natural Exposure of Roofing Materials," presented at the 2010 Passive & Low Energy Cooling for the Built Environment Conference, Rhodes Island, Greece, Oct. 1, 2010.

Mohamad Sleiman, et al., "Accelerated Aging Protocols for Roofing Materials: Version 1.0 (Jul. 2011)," presented at the International Workshop on Advances in Cool Roof Research, Berkeley, CA, Jul. 28, 2011.

R. Levinson and H. Akbari, "Potential benefits of cool roofs on commercial buildings: conserving energy, saving money, and reducing emission of greenhouse gases and air pollutants," Energy Efficiency, 2010, 3:53-109.

R. Levinson, H. Akbari, S. Konopacki, and S. Bretz, "Inclusion of cool roofs in nonresidential Title 24 prescriptive requirements," Energy Policy, 2005, vol. 33, Issue 2, 151-170.

R. Levinson, H. Akbari, P. Berdahl, K. Wood, W. Skilton, and J. Petersheim, "A novel technique for the production of cool colored concrete tile and asphalt shingle roofing products," Solar Energy Materials and Solar Cells, 2010, vol. 94, Issue 6, 946-954.

R. Levinson, P. Berdahl, H. Akbari, W. Miller, I. Joedicke, J. Reilly, Y. Suzuki, and M. Vondran, "Methods of creating solar-reflective nonwhite surfaces and their application to residential roofing materials," Solar Energy Materials and Solar Cells, 2007, vol. 91, Issue 4, 304-314.

D.M. Tobaldi, A. Tucci, G. Camera-Roda, G. Baldi, and L. Esposito, "Photocatalytic activity for exposed building materials," Journal of the European Ceramic Society, 2008, vol. 28, Issue 14, 2645-2652.

F. Arsac, D. Bianchi, J.M. Chovelon, P. Conchon, C. Ferronato, A. Lair, and M. Sleirnan, "Photocatalytic degradation of organic pollutants in water and in air. An analytical approach," Materials Science & Engineering C-Biomimetic and Supramolecular Systems, 2008, vol. 28, Issues 5-6, 722-725.

D. Kibanova, J. Cervini-Silva, and H. Destaillats, "Efficiency of Clay-TiO2 Nanocomposites on the Photocatalytic Elimination of a Model Hydrophobic Air Pollutant," Environmental Science & Technology, 2009, vol. 43, No. 5, 1500-1506.

P. Berdahl, H. Akbari, R. Levinson, and W.A. Miller, "Weathering of roofing materials—An overview," Construction and Building Materials, 2008, vol. 22, Issue 4, 423-433.

T.W. Kirchstetter and T. Novakov, "Controlled generation of black carbon particles from a diffusion flame and applications in evaluating black carbon measurement methods," Atmospheric Environment, 2007, vol. 41, Issue 9, 1874-1888.

R. Levinson, P. Berdahl, A.A. Berhe, and H. Akbari, "Effects of soiling and cleaning on the reflectance and solar heat gain of a light-colored roofing membrane," Atmospheric Environment, 2005, vol. 39, Issue 40 7807-7824.

Mohamad Sleiman, et al., "An update on the development of an accelerated aging method for roofing material," presented at the Asphalt Roofing Manufacturers Association Spring Committee Meeting, Denver, CO, Apr. 16, 2013.

* cited by examiner

MIXTURE AND METHOD FOR SIMULATING SOILING AND WEATHERING OF SURFACES

RELATED APPLICATIONS

This application claims priority to U.S. Provisional Patent Application No. 61/638,949, filed Apr. 26, 2012, which is herein incorporated by reference.

STATEMENT OF GOVERNMENTAL SUPPORT

The invention described and claimed herein was made in part utilizing funds supplied by the U.S. Department of Energy under Contract No. DE-AC02-05CH11231 between the U.S. Department of Energy and the Regents of the University of California for the management and operation of the Lawrence Berkeley National Laboratory. The government has certain rights in this invention.

FIELD

Embodiments disclosed herein relate generally to soiling and weathering of materials. More particularly, some embodiments relate to a composition to be applied to such materials, and some embodiments relate to a method for rapidly (e.g., in a matter of days) simulating the change of radiative properties (e.g., solar reflectance and/or thermal emittance) of roofing materials caused by a number of years (e.g., about three years) of outdoor exposure.

BACKGROUND

The use of highly reflective "cool" roofing materials can save energy used for air conditioning, mitigate urban heat island effects, and improve urban air quality. Replacing a conventional dark roof with a solar-reflective cool roof can reduce a building's annual air conditioning energy use by anywhere from 5% to 20%. Widespread use of cool roofs, by also lowering local outside air temperatures, can further decrease air conditioning energy use by another 10% and reduce the temperature-dependent rate of smog formation. Solar-reflective envelope surfaces can also help contribute to the slowing of global warming. Replacing 10 m$^2$ of dark roofing with white roofing induces a negative radiative forcing in the global atmospheric energy balance sufficient to offset emission of over 2 tonnes of $CO_2$. In all urban areas in hot and temperate regions of the world, the expected emitted $CO_2$ offset for a plausible 0.25 increase in the albedo (i.e., solar reflectance: the ratio of reflected to incident sunlight) of roofs was estimated to be about 70 Gt (gigatonnes) of $CO_2$. Considering that the present annual global $CO_2$ emission is around 30 Gt, installing cool roofs could offset over 2 years of global $CO_2$ emission.

The solar absorptances of building envelope surfaces are often increased by soiling and/or weathering processes, including but not limited to deposition of soot, microbiological growth, and chemical or physical changes induced by exposure to ultraviolet (UV) radiation and outdoor elements. This can increase the need for interior air conditioning by making initially "cool" surfaces hot. It has been found that highly reflective cool roofs lose up to 40% of their initial solar reflectance over time.

SUMMARY

One innovative aspect of the subject matter described in this disclosure can be implemented a mixture including salt, soot, mineral dust, and humic acid. In some embodiments, the mixture includes the salt at about 7% to 31% by weight, the soot at about 1% to 8% by weight, the mineral dust at about 16% to 79% by weight, and the humic acid at about 0% to 69% by weight. In some embodiments, the mixture includes the salt at about 18% to 27% by weight, the soot at about 4% to 12% by weight, the mineral dust at about 28% to 66% by weight, and the humic acid at about 8% to 36% by weight. In some embodiments, each component in the mixture is suspended in an aqueous medium.

Another innovative aspect of the subject matter described in this disclosure can be implemented a method including: (a) weathering a sample of material in a first exposure of the sample to ultraviolet light, water vapor, and elevated temperatures; (b) after operation (a), depositing a soiling mixture on the sample; and (c) after operation (b), weathering the sample in a second exposure of the sample to ultraviolet light, water vapor, and elevated temperatures.

In some embodiments, the first exposure includes heating the sample to about 60° C. for about 8 hours, cooling the sample from about 60° C. to about 50° C., and exposing the sample to water vapor at about 50° C. for about 4 hours. In some embodiments, the ultraviolet light in the first exposure is Ultraviolet A light. In some embodiments, the first exposure is performed twice in a period of about 24 hours.

In some embodiments, the first exposure includes heating the sample to about 55° C. to 65° C. for about 7 hours to 9 hours, cooling the sample from about 55° C. to 65° C. to about 45° C. to 55° C., and exposing the sample to water vapor at about 45° C. to 55° C. for about 3 hours to 5 hours.

In some embodiments, the second exposure includes heating the sample to about 60° C. for about 8 hours, cooling the sample from about 60° C. to about 50° C., and exposing the sample to water vapor at about 50° C. for about 4 hours. In some embodiments, the ultraviolet light in the second exposure is Ultraviolet A light. In some embodiments, the second exposure is performed twice in a period of about 24 hours.

In some embodiments, the sample of material is a roofing material.

In some embodiments, the soiling mixture includes salt, soot, mineral dust, and humic acid. In some embodiments, the soiling mixture includes the salt at about 7% to 31% by weight, the soot at about 1% to 8% by weight, the mineral dust at about 16% to 79% by weight, and the humic acid at about 0% to 69% by weight. In some embodiments, the soiling mixture includes the salt at about 18% to 27% by weight, the soot at about 4% to 12% by weight, the mineral dust at about 28% to 66% by weight, and the humic acid at about 8% to 36% by weight. In some embodiments, each component in the soiling mixture is suspended in an aqueous medium when depositing the soiling mixture on the sample, with the method further including drying the sample after depositing the soiling mixture on the sample.

In some embodiments, operation (b) includes depositing the soiling mixture to substantially uniformly cover a surface of the sample. In some embodiments, operation (b) is performed by spraying the soiling mixture on the sample. In some embodiments, after operation (b), the sample is substantially uniformly covered with agglomerations of the soiling mixture, the agglomerations having a dimension of about 1.5 millimeters to 3 millimeters.

Details of one or more embodiments of the subject matter described in this specification are set forth in the accompanying drawings and the description below. Other features, aspects, and advantages will become apparent from the description, the drawings, and the claims. Note that the relative dimensions of the following figures may not be drawn to scale.

DETAILED DESCRIPTION

Introduction

Figure 1:
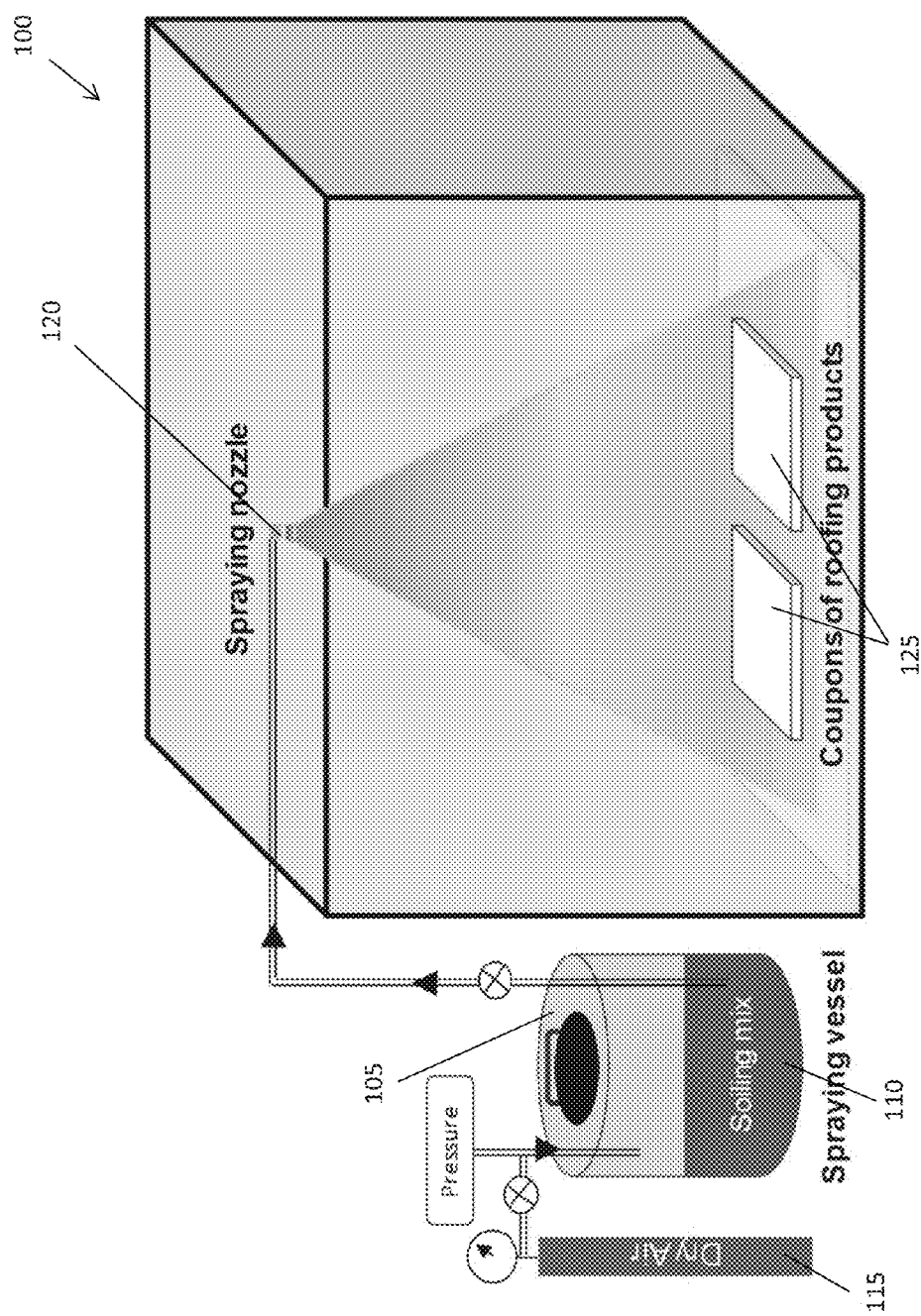
FIG. 1 shows an example of a schematic illustration of a device for the application of soiling agents.
Figure 2:
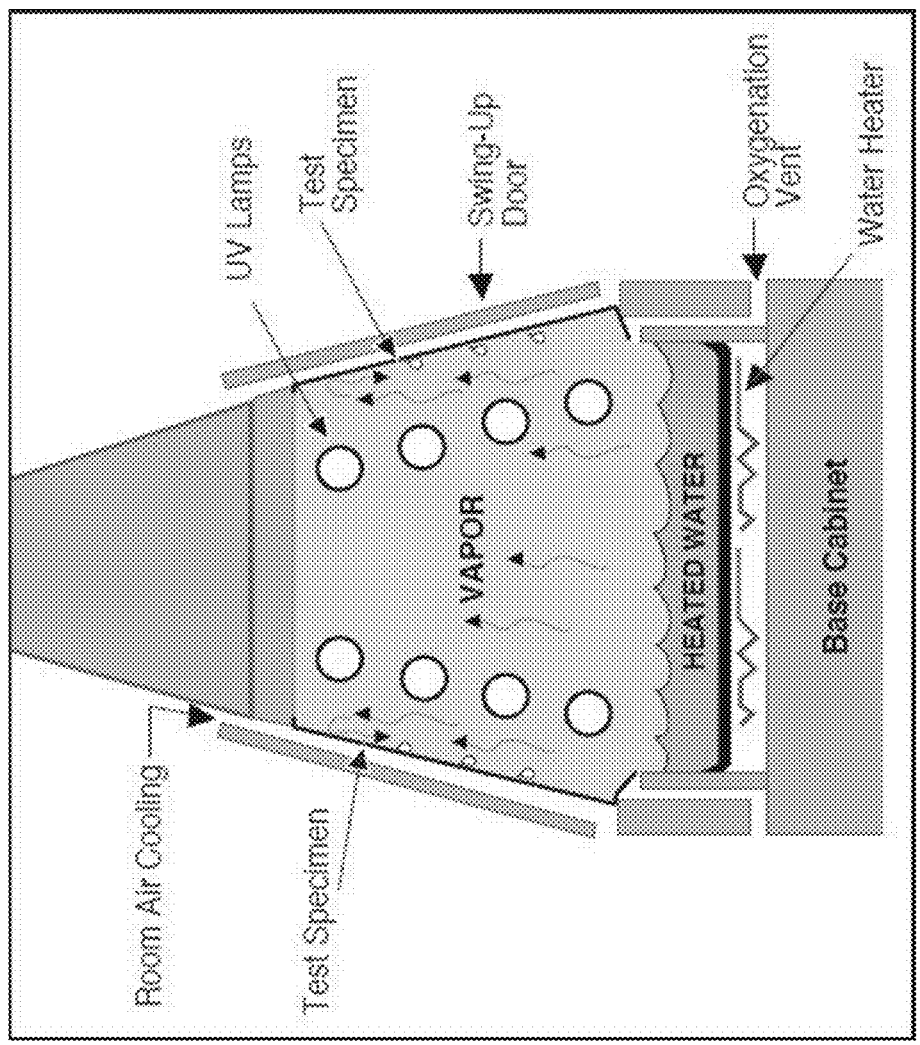
FIG. 2 shows an example of a cross-sectional schematic illustration of a QUV weathering tester used to simulate outdoor weathering conditions.
Figure 3:
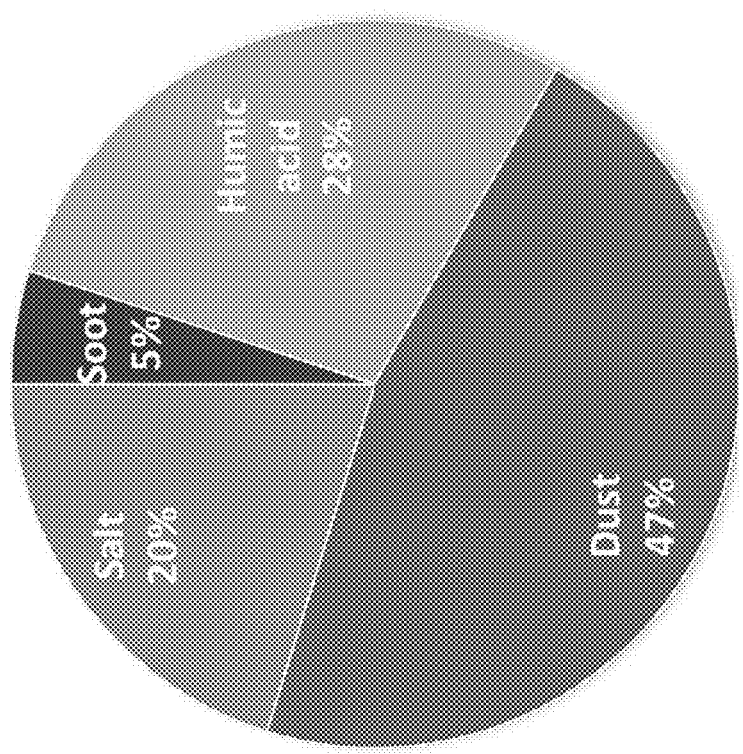
FIG. 3 shows an example of a pie chart of a composition of a soiling mixture for simulating the three year average solar reflectance provided by the CRRC.
Figure 4:
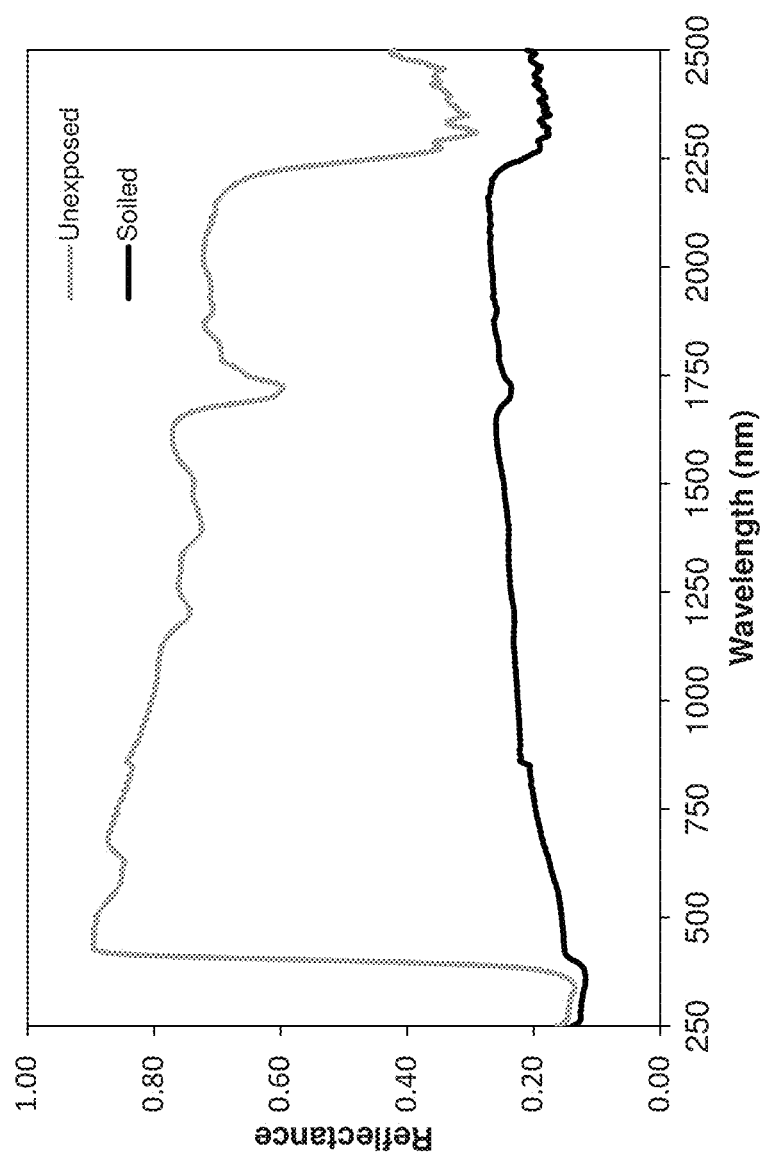
FIG. 4 shows an example of a plot of the solar spectral reflectance of a thick layer of a soiling mixture applied to a white roofing membrane, and compares it to the solar spectral reflectance of the unexposed membrane.
Figure 5:
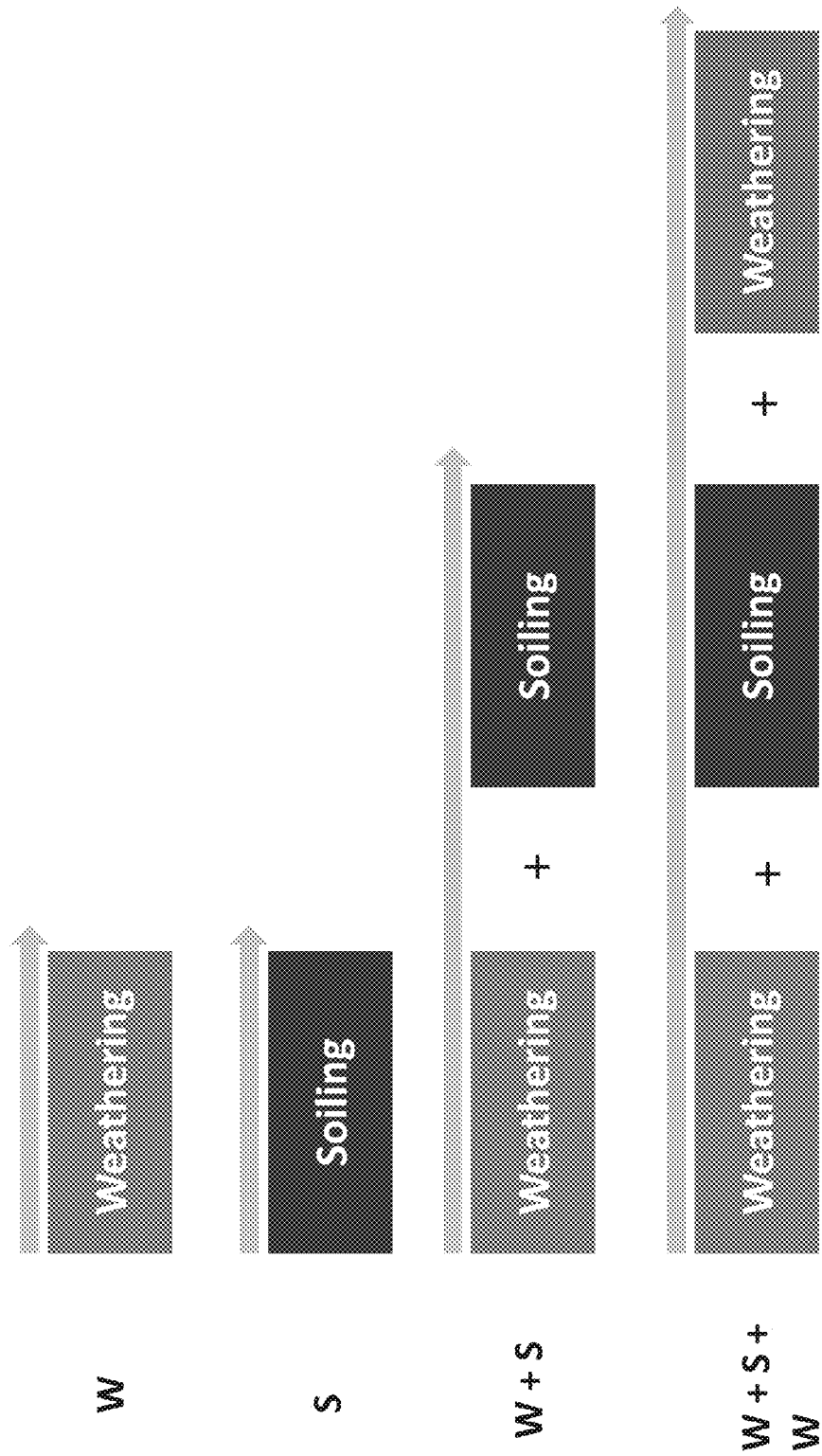
FIG. 5 shows examples of block diagrams illustrating weathering and soiling operations in accelerated aging processes.
Figure 6:
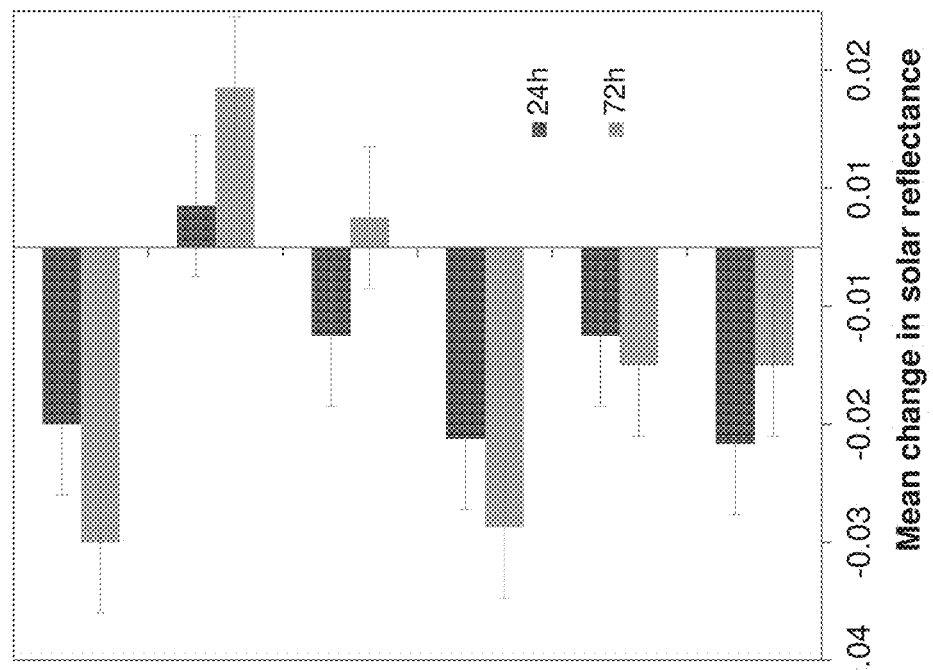
FIG. 6 compares for various roofing materials the mean change in solar reflectance after 24 hours and 72 hours of accelerated weathering.
Figure 7:
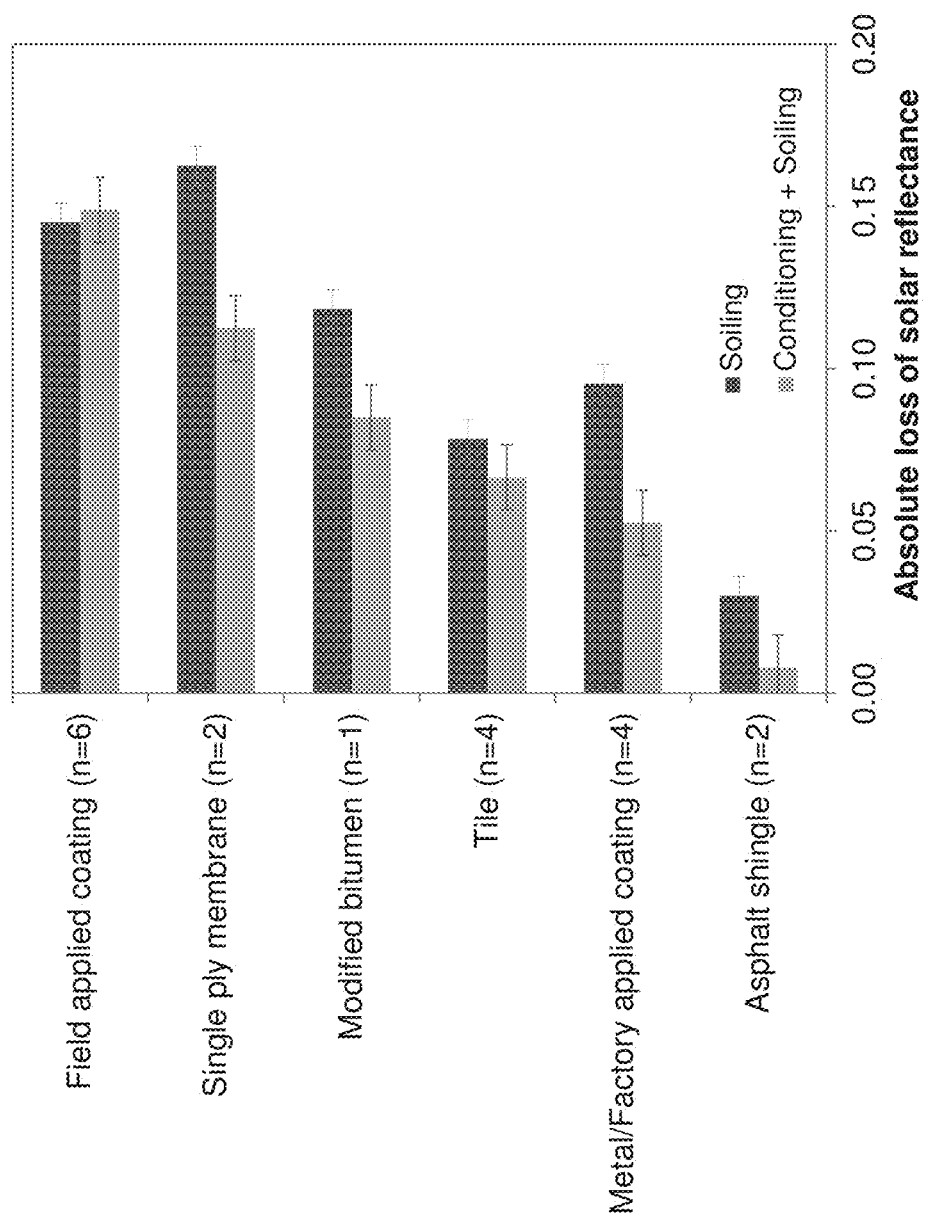
FIG. 7 compares for various roofing materials the absolute loss of solar reflectance after conditioning plus soiling (i.e., soiling preceded by conditioning) to that after soiling alone.
Figure 8:
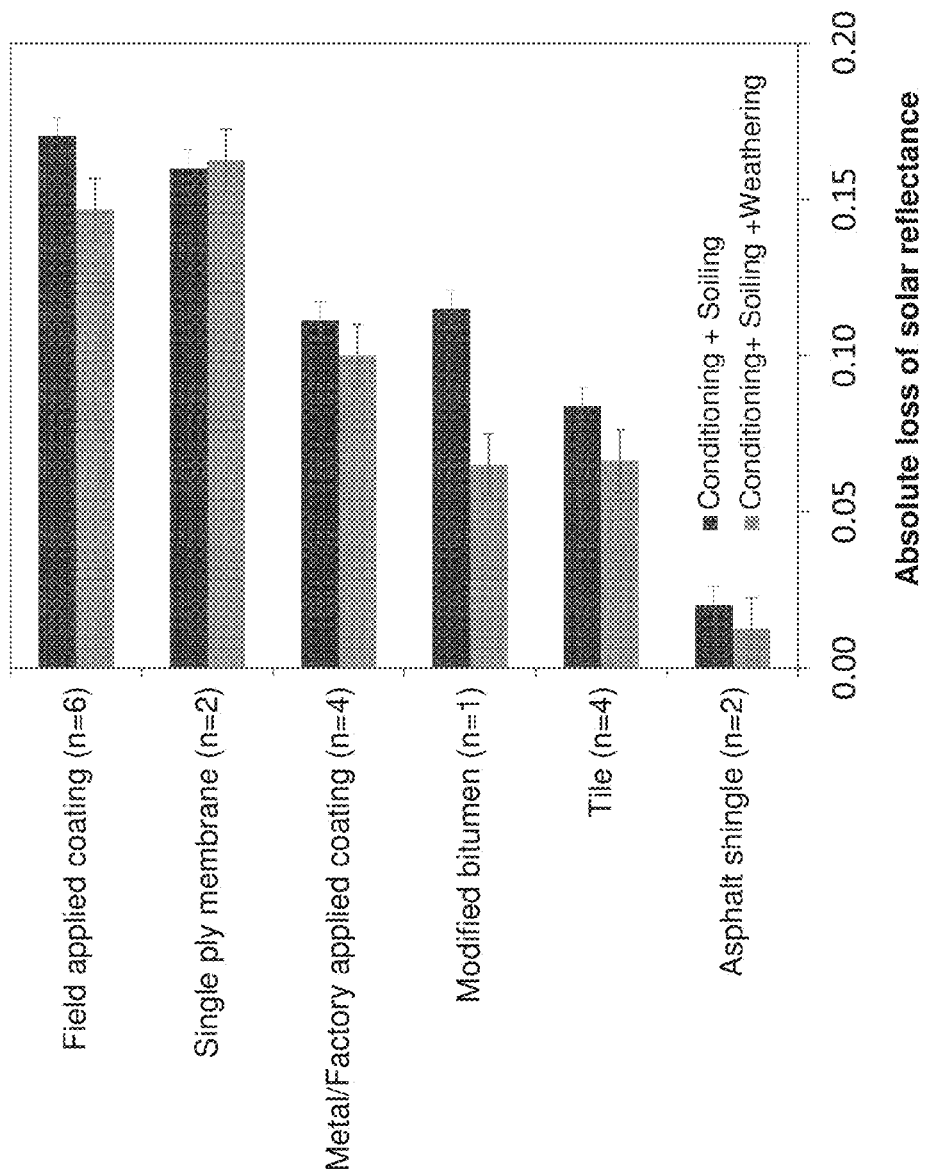
FIG. 8 compares for various roofing materials the absolute loss of solar reflectance after conditioning plus soiling plus weathering to that after conditioning plus soiling.

The advancement of white and cool-colored building materials that improve the radiative properties of urban surfaces, as well as of materials provided with photoactive additives that impart self-preserving properties, has prompted the need for development of reliable accelerated methods for simulating soiling performance under controlled conditions.

The U.S. Cool Roof Rating Council (CRRC) has developed a product rating program which requires roofing manufacturers to report the "aged" values of solar reflectance and thermal emittance measured after three years of natural exposure. Currently, three U.S. climate areas (hot and humid, hot and dry, temperate and polluted) have been designated. Details of the program can be found on the CRRC website. The designated areas are Phoenix, Ariz. (hot and dry); Miami, Fla. (hot and humid); and Youngstown, Ohio (temperate and polluted). Racks designed to hold materials for exposure to the elements for the requisite period of time are located at these designated areas.

A drawback of the current CRRC methodology is that it takes three years to obtain aged solar reflectance ratings. Thus, a company seeking to improve existing materials or to develop new materials by changing formulations needs to wait up to three years to gauge the long term impact of such changes. Accordingly, there is a need to accelerate the process, which in turn can expedite the introduction of new products to market. What is needed then is the development of laboratory soiling and weathering processes that can be applied to roofs and other building envelope surface materials such that their three-year-aged radiative properties can be determined within days or weeks, rather than years.

As described herein, a laboratory method for weathering and soiling that simulates the natural aging processes has been developed. The method allows researchers and manufacturers to assess the long-term radiative properties of building products, and to assess the efficacy of self-cleaning additives and coatings, on the order of days, rather than years. Described herein is the development of an aging process that includes spraying an aqueous suspension of soot, mineral dust, and soluble soiling constituents such as salts and organic matter surrogates (e.g., humic acid) on materials (e.g., roofing materials). In some embodiments, specific compositions/mixtures have been developed for this process. In some embodiments, different compositions/mixtures have been developed for simulating each of three U.S. locations mandated by the U.S. Cool Roof Rating Council (CRRC) rating program.

In some embodiments, a method includes spraying of a composition/mixture onto a sample or coupon, and then weathering the coated coupon in an accelerated weathering device.

In some embodiments, a method includes first weathering ("conditioning") a sample of material in an accelerated weathering device, depositing a mixture of soiling agents on the sample, and subjecting the sample to a second weathering operation. In some embodiments, each of the two weathering operations is carried out for 24 hours or about 24 hours. In some embodiments, both the first and second weathering operations include two operations where for each 12 hour or about 12 hour operation, the sample is subjected to heat under Ultraviolet A light (about 400 nm to 315 nm, UVA) at about 60° C. for a period of 8 hours or about 8 hours, and then exposed to water vapor at about 50° C. for 4 hours or about 4 hours.

In some embodiments, the method includes using a spray nozzle to form fine droplet sprays that are deposited on the surface of a sample of the material to be tested, with spraying performed until the surface of the sample is uniformly covered. In some embodiments, about 40% to 60% of the surface is covered. Once coated, the sample is dried under a NIR heat lamp, then placed in an accelerated weathering device and exposed to UV light, heat, and water, to simulate outdoor weathering. In some embodiments, the accelerated weathering device chamber is heated to about 60° C. during UV light irradiation. The sample is then cooled to about 50° C. to induce condensation of water vapor to simulate weathering, which may wash off a portion of the soiling mixture.

The embodiments disclosed herein also may be applicable to the soiling and weathering of different materials, including photovoltaics, pavements, and painted surfaces, for example.

Preparation of Soiling Agents

Atmospheric particles originate from windblown dust, forest and grassland fires, living vegetation, and sea spray, as well as from human activities, such as the burning of fossil and biomass fuels. They are also formed in the atmosphere via chemical reactions that convert gaseous precursors to condensed phase particles. All particles scatter sunlight and some weakly absorb sunlight. A notable exception is black carbonaceous soot emitted from the burning of fossil and biomass fuels and from fires. Because of its strong mass absorption efficiency, small amounts of black soot may appreciably contribute to reduction of solar reflectance of building surfaces. Given the diversity of soiling agents associated with climate, geographic conditions, season, and patterns of human activities, an aqueous suspension of four soiling agents may be used for the accelerated testing, as set forth below. The choice of soiling agents and their relative composition was made based on their respective contribution to changes in the solar reflectance spectra of soiled surfaces, determined in the laboratory. These same selected soiling agents have also been shown to accumulate on surfaces exposed in natural outdoor settings.

It is to be understood that the mixing amounts and ratios provided below are provided by way of example only, and are not to be considered as limiting of the embodiments disclosed herein.

Sooty Particles. Roofing materials are coated with hydrophilic soot that is dispersible in water. A self-dispersible soot that is commercially available can be used (e.g., AquaBlack 001, Tokai Carbon Co., LTD, Tokyo, Japan). Alternatively, soot can be generated using a diffusion flame and collected on a Teflon membrane. This freshly produced soot is then transformed from hydrophobic to hydrophilic by exposing it to ozone, after which the soot is mixed into water to form stable aqueous suspensions.

In some embodiments, the hydrophilic soot produced by a methane diffusion flame after ozonation is collected on polytetrafluoroethylene (e.g., Teflon, by E. I. du Pont de Nemours and Company of Wilmington, Del.) filters. Then, the soot is rinsed off the filter and into a water reservoir with a gentle stream of water (e.g., using a squirt bottle). The mass of black carbon soot added to the water reservoir is the difference in the dry masses of the Teflon filter before and after rinsing away the black carbon soot. Typically, 0.25 gram (g) of soot is collected into 1 liter (L) of distilled water and stirred for few minutes to produce a stable suspension of 0.25 g/L. Stirring is repeated prior to utilization of the suspension if it has been sitting in the lab for longer than 1 hour in order to prevent sedimentation.

Mineral dust. A mixture of iron oxide ($Fe_2O_3$) powder (e.g., less than 5 μm particle size) and two natural clays, montmorillonite and hydrophilic bentonite, can be used to represent the dusting agent. Typically, 0.3 g of $Fe_2O_3$ powder is mixed with 1 g of bentonite and 1 g of montmorillonite. Then, the mixture is transferred into 1 L of distilled water and stirred for about 1 hour to prepare a suspension of 2.3 g/L. Stirring is repeated prior to utilization of the suspension if it has been sitting in the lab for longer than 1 hour in order to prevent sedimentation.

Salty particles. A 1 L solution containing a mixture of inorganic salts is prepared by dissolving 0.3 g of sodium chloride (NaCl), 0.3 g of sodium nitrate ($NaNO_3$) and 0.4 g of calcium sulfate dihydrate ($CaSO_4.2H_2O$). The total salt concentration of the solution is 1.0 g/L.

Particulate organic matter. 1.4 grams of commercially available humic acid is dissolved in 1 L of distilled water to produce a solution of 1.4 g/L. Atmospheric aerosol particles typically contain between 5% and 40% (by weight) of a mixture of oxidized polymeric organic compounds that absorb solar radiation. Humic acids are good surrogates for those compounds. In addition, the chemical structure of these acids is comparable to decomposition products and residues from microbiological soiling agents such as algae, bacteria, and fungi.

In some embodiments, separate solutions/suspensions are prepared for each category of material. Once prepared, the individual components can be mixed together in various ratios depending upon the climate zone to be simulated. By way of example, to simulate the average change in solar reflectance (SR) for the 3 CRRC sites, a 1 L mixture is prepared by adding 250 mL of each individual component previously prepared as above described. This gives the following final concentrations: dust (0.575 g/L), salts (0.25 g/L), humic acid (0.35 g/L), and soot (0.0625 g/L).

In some embodiments, the soiling mixtures are prepared and stored separately so that the relative compositions can be easily adjusted for any given experiment to simulate exposure locations within the U.S., as well as outside, without having to prepare new mixtures of individual components. In the examples that follow, it is to be appreciated that the methods used are examples, and other ways of mixing the various ingredients are contemplated.

Application of Soiling Agents

A device for spraying an aqueous suspension of soot and other soluble soiling constituents such as salts (e.g., calcium sulfate, sodium nitrate, sodium chloride, and the like) and organic matter surrogates (e.g., humic acid, as well as other Humic Like Substances) is illustrated in FIG. 1. The device 100 includes a vessel 105, containing an aqueous suspension of soiling agents 110, which is pressurized with air 115 and connected to a nozzle 120 that sprays droplets onto the surface of roofing materials 125.

More specifically, in a typical experiment, the calibration of the spraying is carried out using a roofing reference specimen (10 cm×10 cm), such as a single ply membrane, for example. The specimen is weighed (mass: M0) immediately before soiling. The spray is turned on for about 10 seconds to 15 seconds to reach a uniform and stable spraying pattern. Then, the weighed coupon is introduced into the soiling chamber, while the spray nozzle is still on, and placed at a determined position (about a 40 cm to 60 cm vertical distance from spraying nozzle) to optimize the surface coverage (e.g., the droplet size is the most uniform at this position). After about 10 seconds of spraying, the specimen is removed from the chamber and subsequently weighed (mass: M1). Typically, the soiling mass including water retained by the reference specimen (M1−M0) should be about 0.7 g to 0.9 g or equivalent surface coverage of about 7 mg $cm^{-2}$ to 9 mg $cm^{-2}$.

Once the calibration is achieved by obtaining a uniform coverage of soiling spots (i.e., agglomerations of the soiling material) and the right mass of soiling, the soiling procedure can be applied to the specimens (10 cm×10 cm) that are to be tested, using the calibrated conditions of spraying (duration, position). Typically, the spraying procedure is repeated three times for each material, with one specimen soiled at a time.

After spraying, each specimen is dried with a Near Infrared (NIR) heat lamp. The duration of drying depends on the roofing material, the radiance from the lamp, and the distance of specimen from the lamp. Typically, the drying time is about 2 minutes to 15 minutes.

Figure 9:
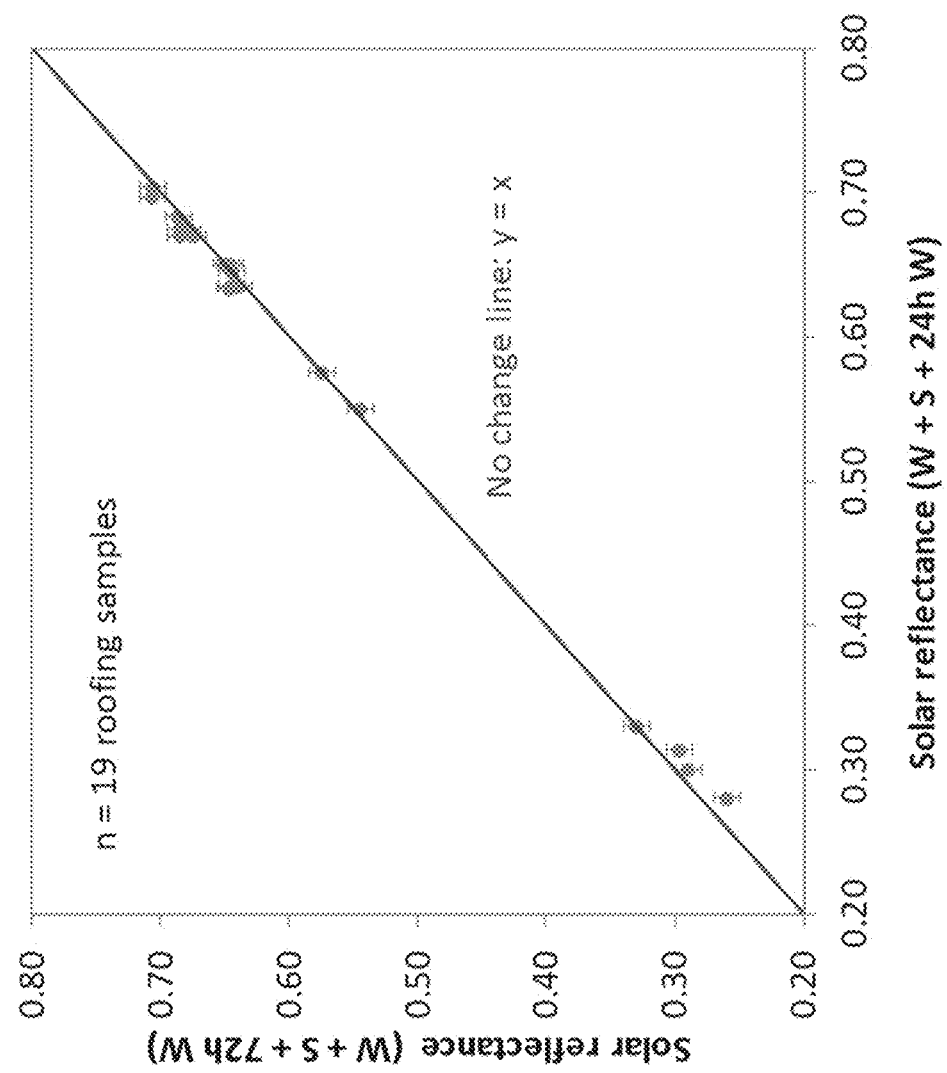
FIG. 9 shows an example of plot showing the effect of increasing the duration of weathering after soiling to 72 hours from 24 hours.

In various experiments, different sizes of nozzle openings were tested at various pressures and uniformity was measured. This was determined by measuring solar reflectance at three surface locations and averaging. An acceptable variation between locations was found to be no greater than 5%. In the spray apparatus shown in FIG. 1 used to coat the specimens of the illustrative examples, a SF-2 spray nozzle (from Spraying Systems Co., Wheaton, Ill.) was used to produce a hollow cone-type spray with droplet sizes of about 100 μm to 200 μm when the spray gun was operated at about 16 psig to 18 psig. Again, neither the exact size of the spray droplets nor the pressure at which they are applied is important in some embodiments; what is important, however, is that the droplets not run off the sprayed surfaces and that the soiling coverage on the surface is substantially uniform, with soiling spots that are about 1.5 mm to 3.0 mm in diameter. In the experiments hereinafter described, roofing material specimens of 10 cm×10 cm were sprayed with about 1 gram of the aqueous soiling mixture, with the amounts confirmed by weighing of the coupons both before and after spraying.

In the experiments run in a laboratory, spraying times for the soil mixture were about 5 seconds to 30 seconds.

Simulation of Outdoor Weathering

To simulate outdoor weathering, a weathering device, which may be referred to as a weatherometer, may be used. As used herein, a weathering device refers generally to a device in which specimen materials can be subjected to simulated conditions, such as expose to the sun, rain, and temperature changes. The simulated conditions are usually obtained by the use of electric arcs, heating elements, and water sprays. Such equipment is commercially available.

For the reported experiments, a QUV weathering tester (see FIG. 2), purchased from Q-Lab Corporation (Westlake, Ohio) was used. Though not shown in the figure, the QUV weathering tester includes spray nozzles, and is capable of operating in spray and/or condensation mode. Herein, the condensation option was used, and in some embodiments, the chamber was heated to about 60° C. during UV irradiation, and then cooled to about 50° C. to induce condensation of water vapor. The materials were exposed to alternating cycles of UV light and moisture at controlled, elevated temperatures to simulate the effects of sunlight, and to water condensation to simulate dew and rain. Cycle 1 of ASTM G154 (Standard Practice for Operating Fluorescent Light Apparatus for UV Exposure of Nonmetallic Materials), hereafter designed ASTM G154, was used as the standard testing method. All reported weathering experiments herein were run for 24 hours (i.e., 2 cycles of 12 hours using ASTM G154), which corresponds to two cycles of ASTM G154. Each cycle included 8 hours UVA irradiation at 60° C. and 4 hours of water condensation at 50° C.

Soiling Mixture

In one study, it was shown that natural soiling of glass exposed for two years in six European cities contained four major constituents: dust minerals (28% to 66%), black carbon (4% to 12%), particulate organic matter (8% to 36%), and soluble salts (18% to 27%). Considering the variability of sources and climatologic conditions in the study, the composition was relatively consistent across the six sampling sites. Based on this data, a standard mixture of four soiling ingredients was prepared that represent the average composition and used to simulate the three year average solar reflectance of roofing materials aged for three years at the three CRRC locations. The composition of this mixture is shown in the FIG. 3 pie chart: dust (47%), salts (20%), humic acid (28%) and soot (5%). This corresponds to dust (0.575 g/L), salts (0.25 g/L), humic acid (0.35 g/L) and soot (0.0625 g/L). Other combinations are shown in FIG. 14, in which relative compositions of soiling mixtures are shown for the three specific U.S. exposure locations.

To measure the solar reflectance of the soiling mixture, a thick layer of this mixture was applied to a roofing material to thoroughly cover the underlying color of the material. Testing showed that the solar reflectance of this mixture is very similar to the typical solar reflectance (e.g., 0.2-0.3) for a thick, natural opaque soil layer (See FIG. 4).

Selection of Roofing Products to Evaluate the Accelerated Aging Process 100 roofing materials from 40 industrial manufacturers were screened. After screening, six categories of roofing materials that represent the majority of the U.S. roofing market were selected. The selection criteria included diversity of products and colors, market presence, sample uniformity, and availability of aged samples. The six categories were asphalt shingle (n=2), tile (n=4), single ply membrane (n=2), field applied coating (n=6), metal/factory applied coating (n=4), and modified bitumen (n=1), wherein n is the number of products that were tested within a given category of roofing materials.

Natural Aging

To simulate natural aging, different approaches were tested to study the effect of simulated soiling, accelerated weathering, and combinations of weathering and soiling in cycles (See FIG. 5). The effect of accelerated weathering on the solar reflectance (SR) of selected roofing samples was tested using the QUV. The weathering was carried out following ASTM G154. FIG. 6 shows the effect of 24 hours and 72 hours of accelerated weathering on the loss of solar reflectance of various roofing products. Overall, the effect was very small (−0.03 to 0.01) for all categories. The SR of most samples decreased except for the asphalt shingle.

Effect of Weathering Before Soiling (i.e., Conditioning) and After Soiling

Although weathering alone did not significantly influence the solar reflectance of roofing samples, the effect of weathering before soiling on the adherence of soiling constituents was investigated.

The results are shown in FIG. 7, which shows that the loss of solar reflectance was less pronounced for most samples if a pre-weathering step (24 h, ASTM G154) is performed before soiling. This means that the pre-weathering step reduced the adherence of soiling constituents to the surface of roofing samples. As consequence, a pre-weathering (i.e., conditioning) step may be important to be included in the accelerated aging process.

Given that conditioning (i.e., weathering before soiling) affects the adherence of the soiling constituents, the effect of adding a weathering step after soiling was studied to evaluate if the surface of roofing materials will be cleaned or not (FIG. 8). Results showed that for all samples, post-weathering (24 h, ASTM G154) helped to partially clean the surface of roofing samples by removing some of the soiling constituents, which reduced the loss of solar reflectance.

This finding led to the investigation of longer weathering durations to determine if extended weathering could clean completely the surface of soiled samples. FIG. 9 shows the solar reflectance of samples weathered for 72 hours versus 24 hours after being exposed to pre-weathering (24 h, ASTM G154) and soiling (the standard mixture) under identical experimental conditions. The linear correlation (1:1) shows that increasing weathering duration from 24 hours to 72 hours did not affect the loss of SR due to soiling. Thus, it appears that a fraction of the soiling deposit can be removed during weathering whereas the remaining components adhere well to the surface of roofing materials. As consequence, in some embodiments there is no need to use more than 24 hours of weathering as part of the accelerated aging process.

Simulated Aging Process

Figure 10A:
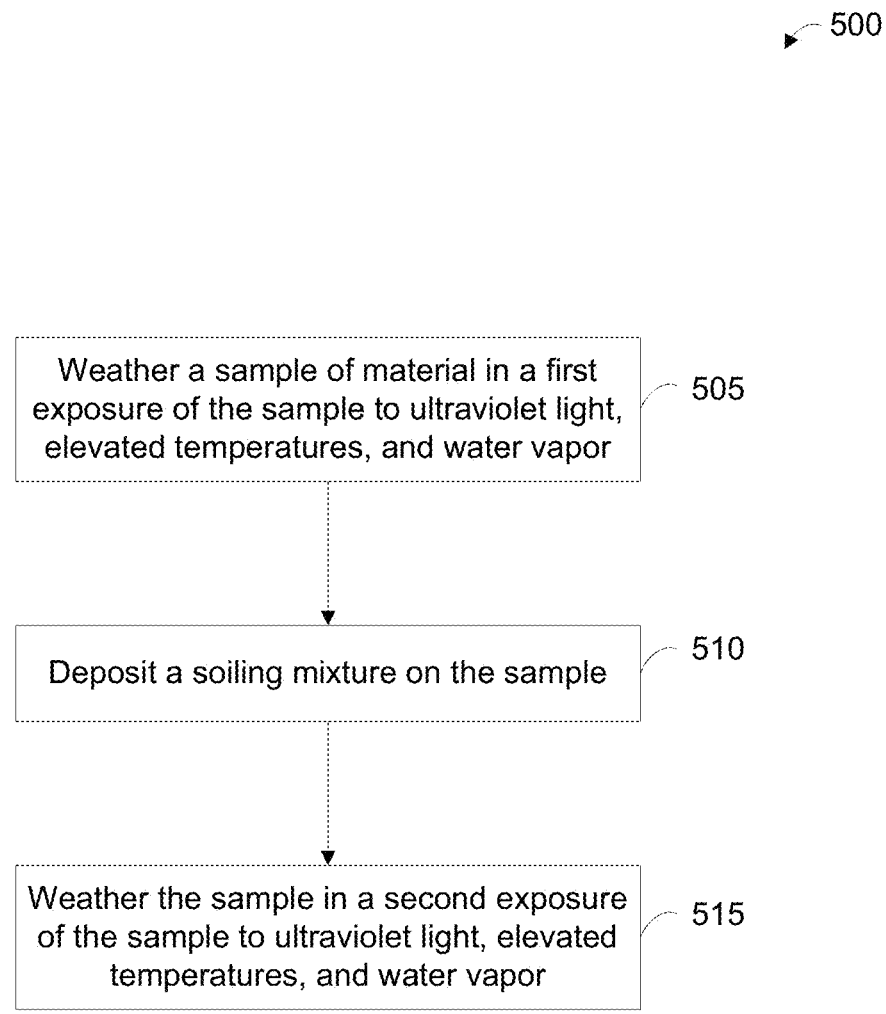
FIG. 10A shows an example of a flow diagram illustrating a process for simulating natural aging of a sample.

Based on the results presented above, a defined simulated aging process was developed. FIG. 10A shows an example of a flow diagram illustrating a process for simulating natural aging of a sample. At block 505 of the process 500, a sample of material is weathered in a first exposure of the sample to ultraviolet light, elevated temperatures, and water vapor. At block 510, a soiling mixture is deposited on the sample. At block 515, the sample is weathered in a second exposure of the sample to ultraviolet light, elevated temperatures and water vapor.

Figure 10B:
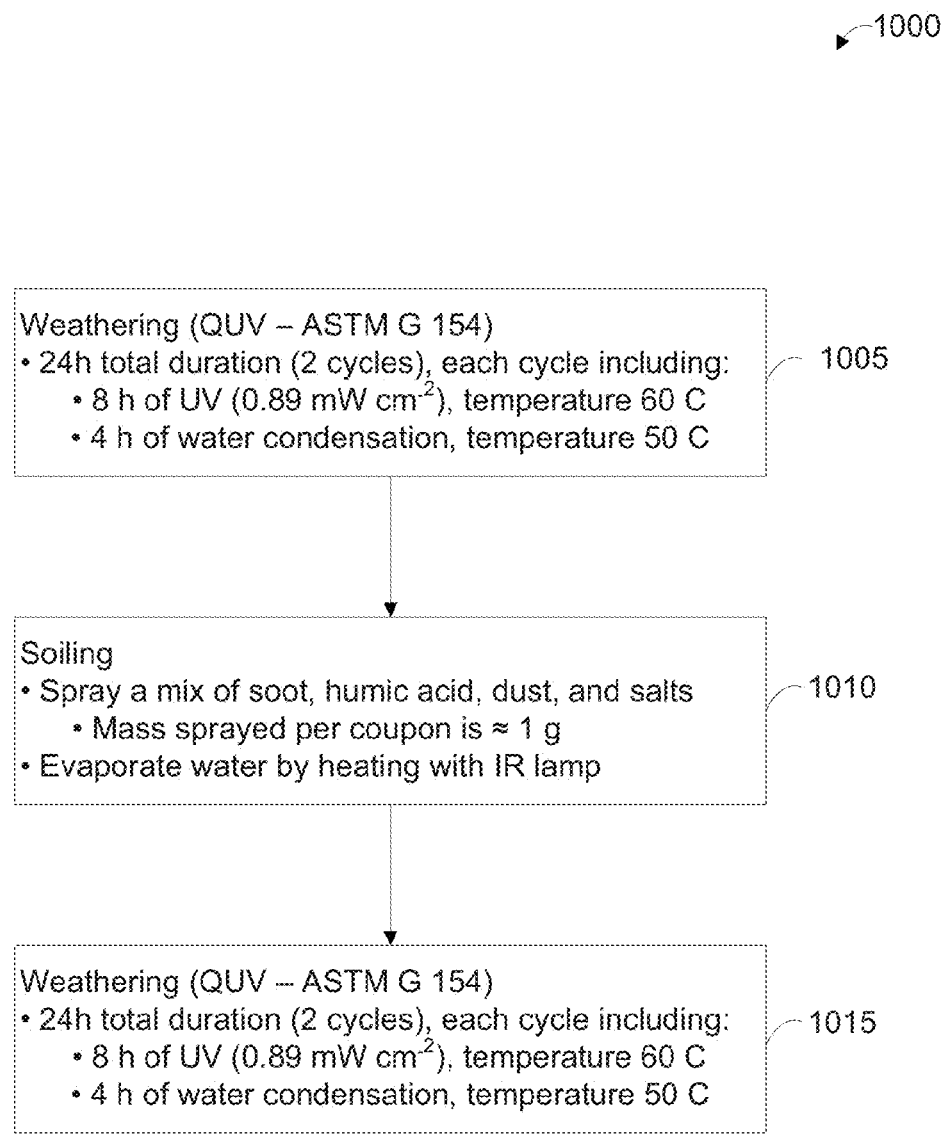
FIG. 10B shows an example of a flow diagram illustrating a process for simulating natural aging of a sample.

FIG. 10B shows an example of a flow diagram illustrating a process for simulating natural aging of a sample. By this process (1000), a first weathering operation (block 1005) is performed over a 24 hour period, using two cycles where in each cycle coupons of roofing material are exposed to UVA at 60° C. for 8 hours, followed by exposure to water vapor at 50° C. for 4 hours (e.g., in the QUV apparatus previously described). The same weathering operation is performed again (block 1015) in the simulated aging process after the soiling operation (block 1010).

Figure 11:
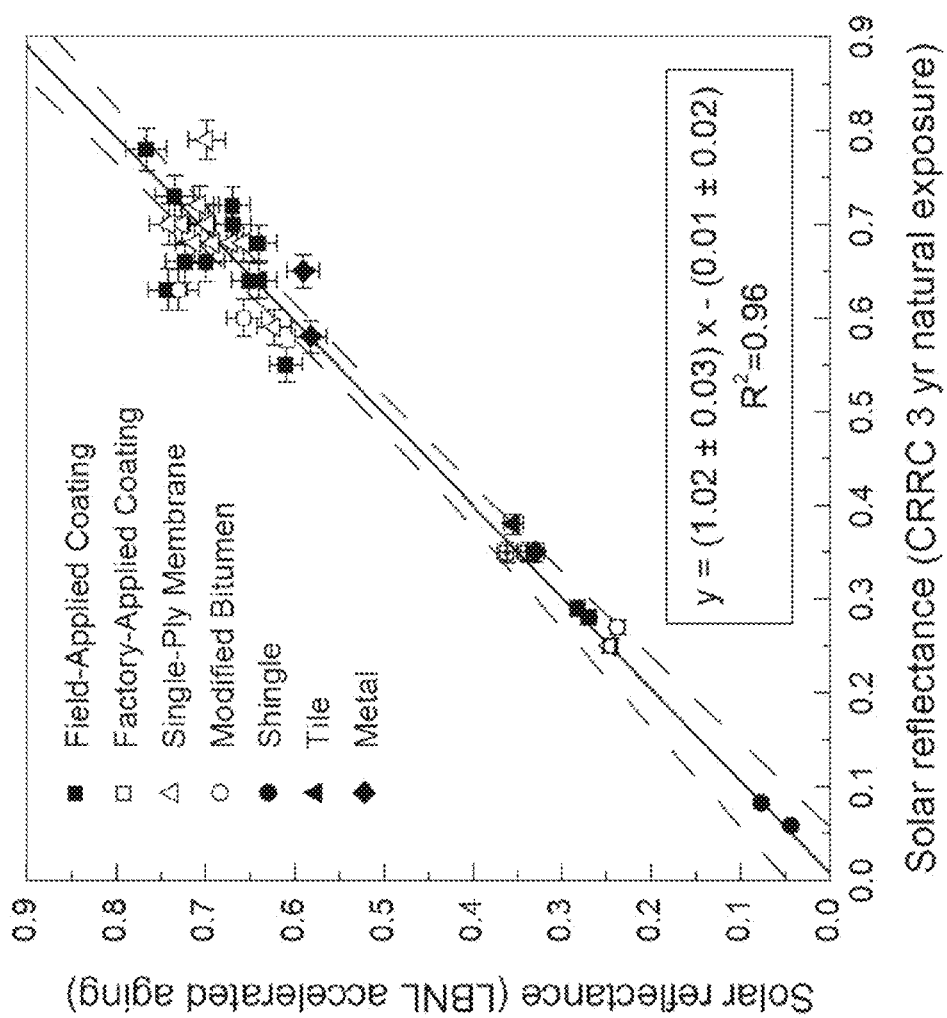
FIG. 11 shows an example of plot of CRRC three year aged solar reflectance data versus solar reflectance using data obtained following the process shown in FIG. 10B.

To validate the simulated aging process 1000 shown in FIG. 10B, the average solar reflectance reported by the CRRC for a number of roofing samples for 3 years that had been exposed in the three U.S. locations (Ohio, Arizona, Florida) was compared with the solar reflectance of the same samples exposed in the laboratory using the experimental process shown in FIG. 10B. FIG. 11 shows a good match between the results obtained in the laboratory and those reported by the CRRC, validating that the accelerated aging process of the embodiments disclosed herein can simulate in few days the change in solar reflectance due to three years of natural aging of roofing materials.

Figure 12:
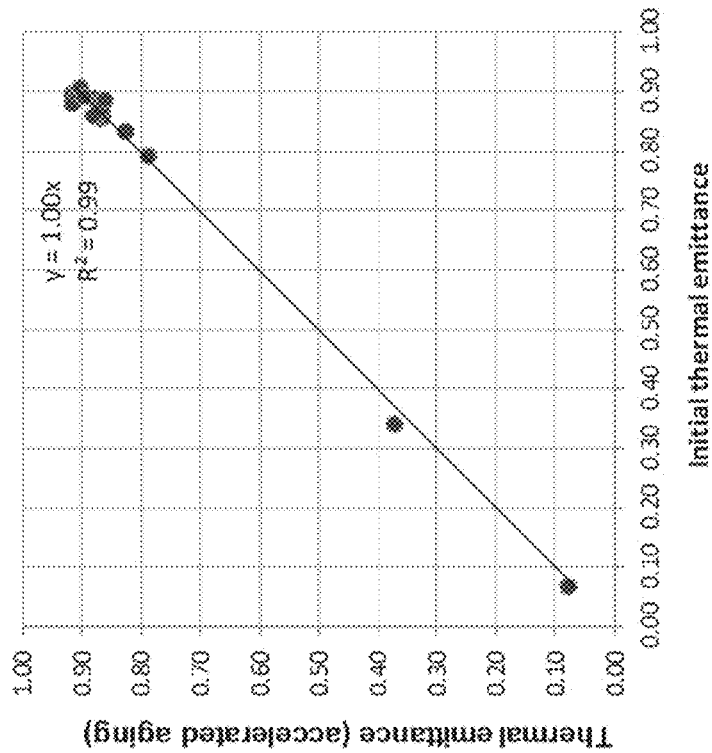
FIG. 12 shows the thermal emittance of 13 roofing products obtained by the accelerated simulated field exposure method versus CRRC 3 year thermal emittance rating.
Figure 12:
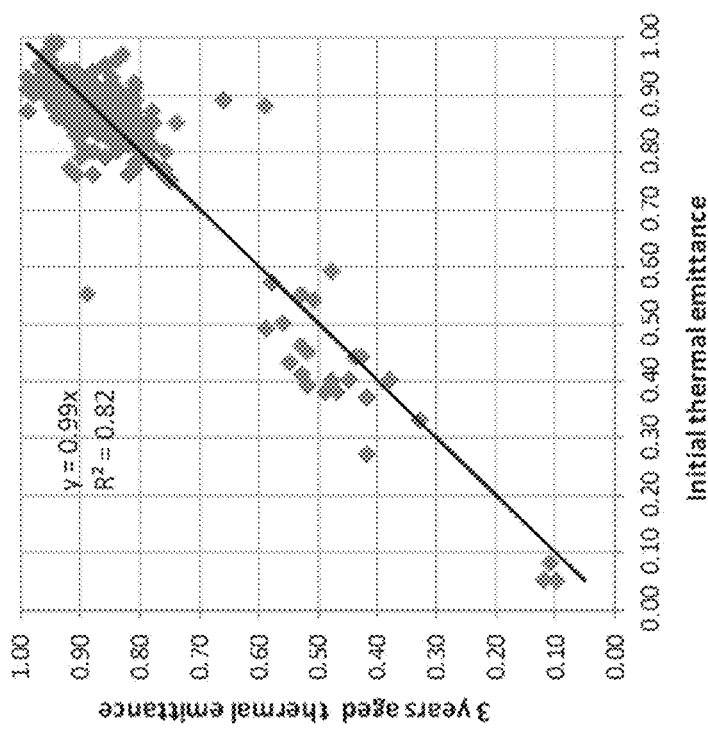

The thermal emittances of 28 diverse roofing products exposed using the procedure described with respect to FIG. 10B were compared with three-site-averaged 3-year aged thermal emittances reported by the CRRC (see FIG. 12). Thermal emittance was measured following ASTM Standard C1371, as specified by standard CRRC-1. Although the change in thermal emittance is relatively small, the simulated exposure method provides similar trend compared to the CRRC rating data (see FIG. 12).

Figure 13:
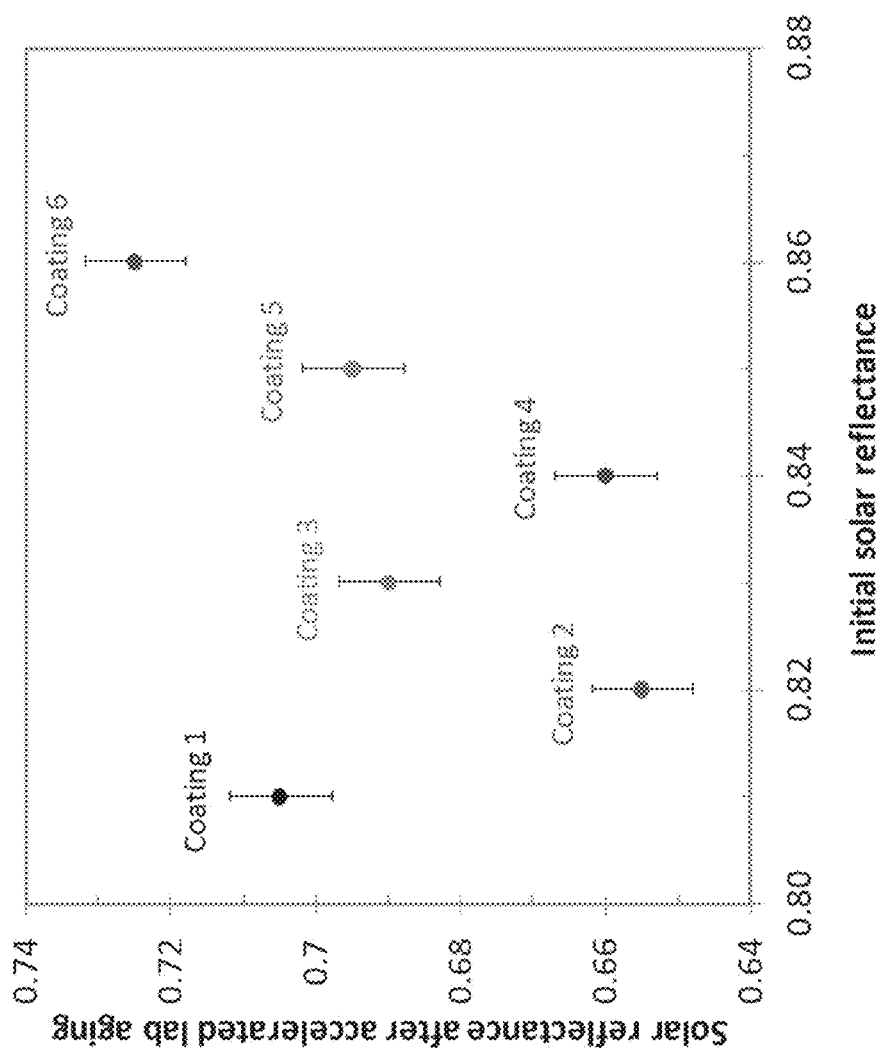
FIG. 13 shows an example of a plot of the material dependence of the accelerated aging process.

Also selected were six different field applied coatings with different initial solar reflectance values to study the material dependence of the accelerated aging process. The results shown in FIG. 13 show that the accelerated aging process leads to different loss of solar reflectance in different coatings. This finding demonstrates that the results of the simulated aging process are material dependent. In other words, the results are governed by the capacity of the roofing material to retain soiling and/or to be cleaned by weathering.

Simulation and Validation of Site-Specific Three Year Aged Solar Reflectance

Figure 14:
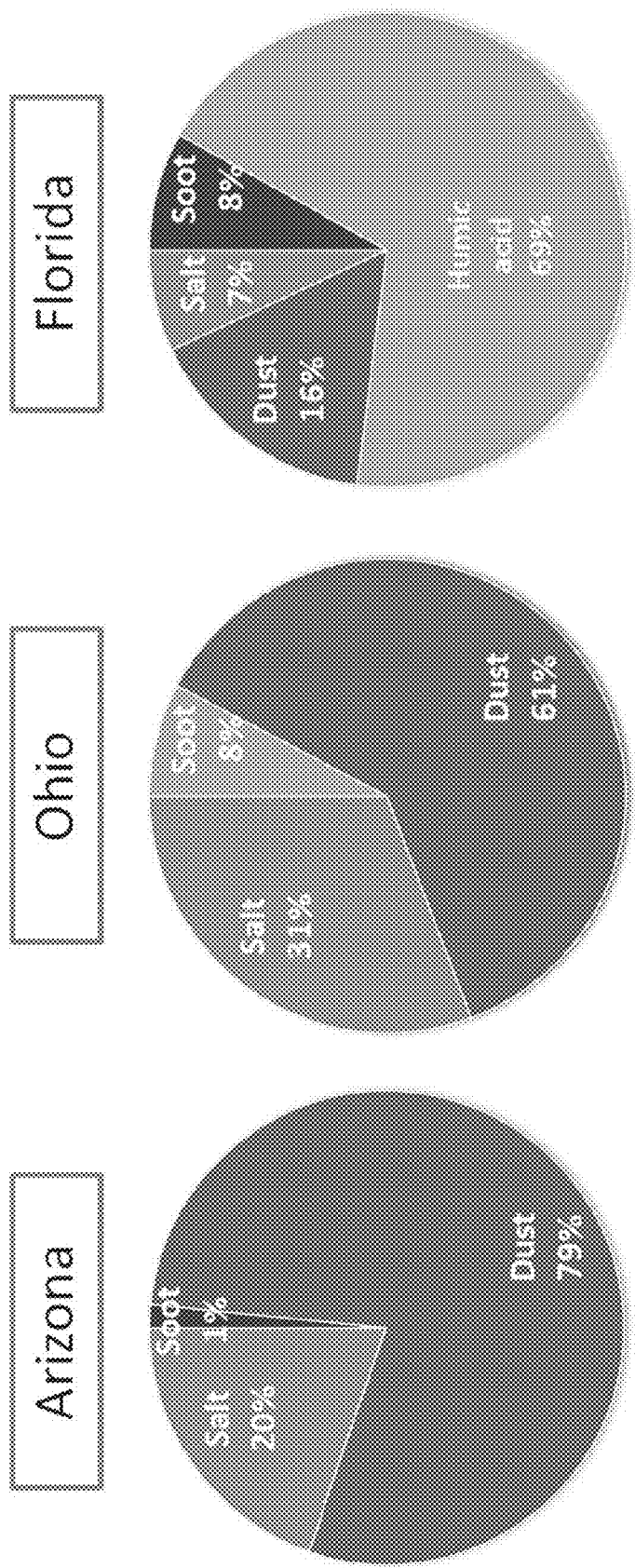
FIG. 14 shows examples of pie charts of the relative compositions of various soiling mixtures for three U.S. exposure locations.

In an attempt to simulate site-specific 3-year aged solar reflectance, three soiling mixtures were prepared by varying the relative proportions or percentages of each of the four soiling components to simulate the natural soiling environment in each of the three CRRC locations (Arizona, Ohio, and Florida). FIG. 14 shows the relative (%) compositions of these mixtures.

The soiling application was identical to the standard process shown in FIG. 10B. In addition, since weathering affects little change in solar reflectance, the same weathering conditions shown in FIG. 10B were used for all three locations.

Figure 15:
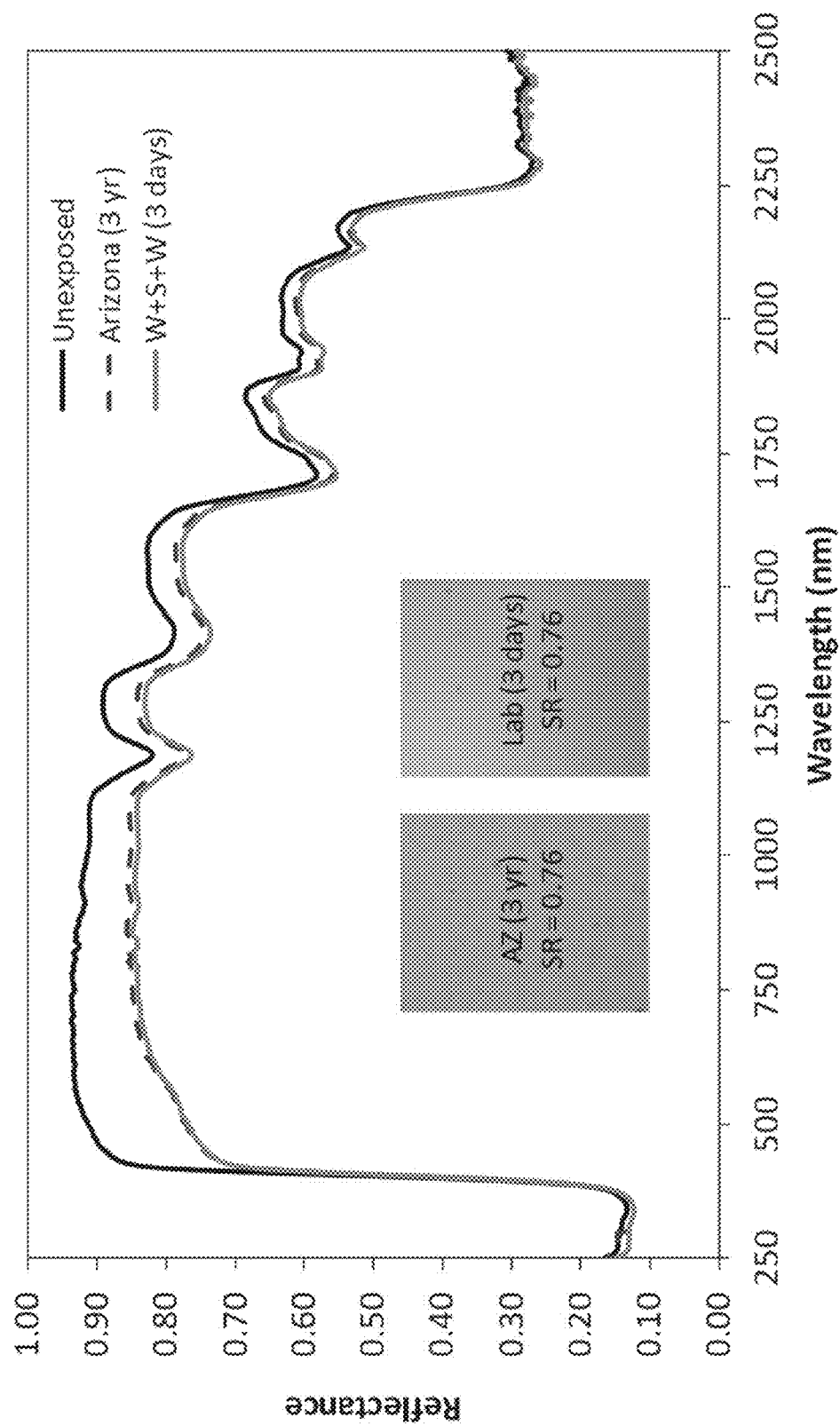
FIGS. 15, 16, 17 and 18 show examples of the solar spectral reflectances of exposed three year aged white field applied coating samples compared to laboratory data generated using the accelerated aging method shown in FIG. 10B, employing the appropriate location specific soiling mixtures shown in FIG. 14.
Figure 16:
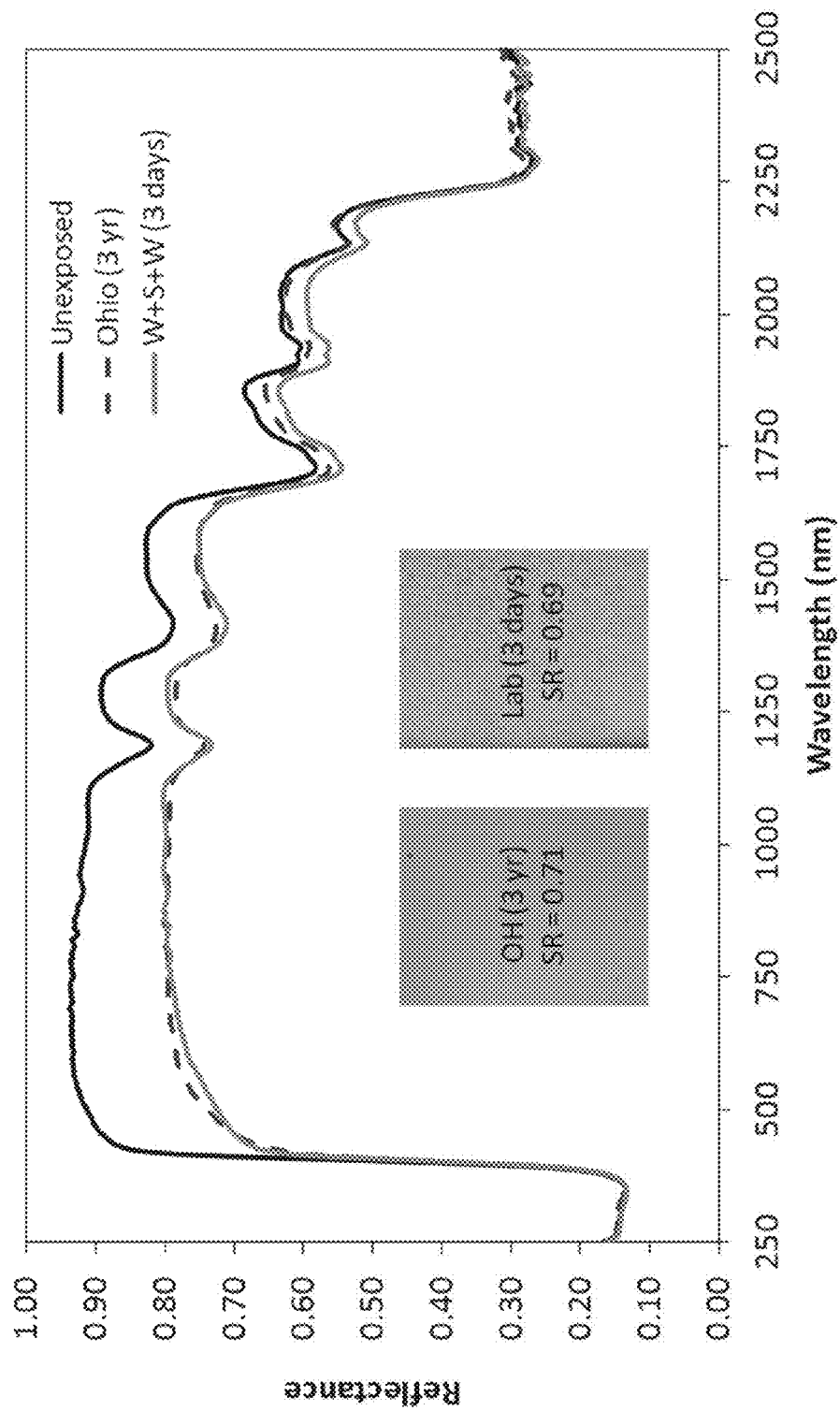
Figure 17:
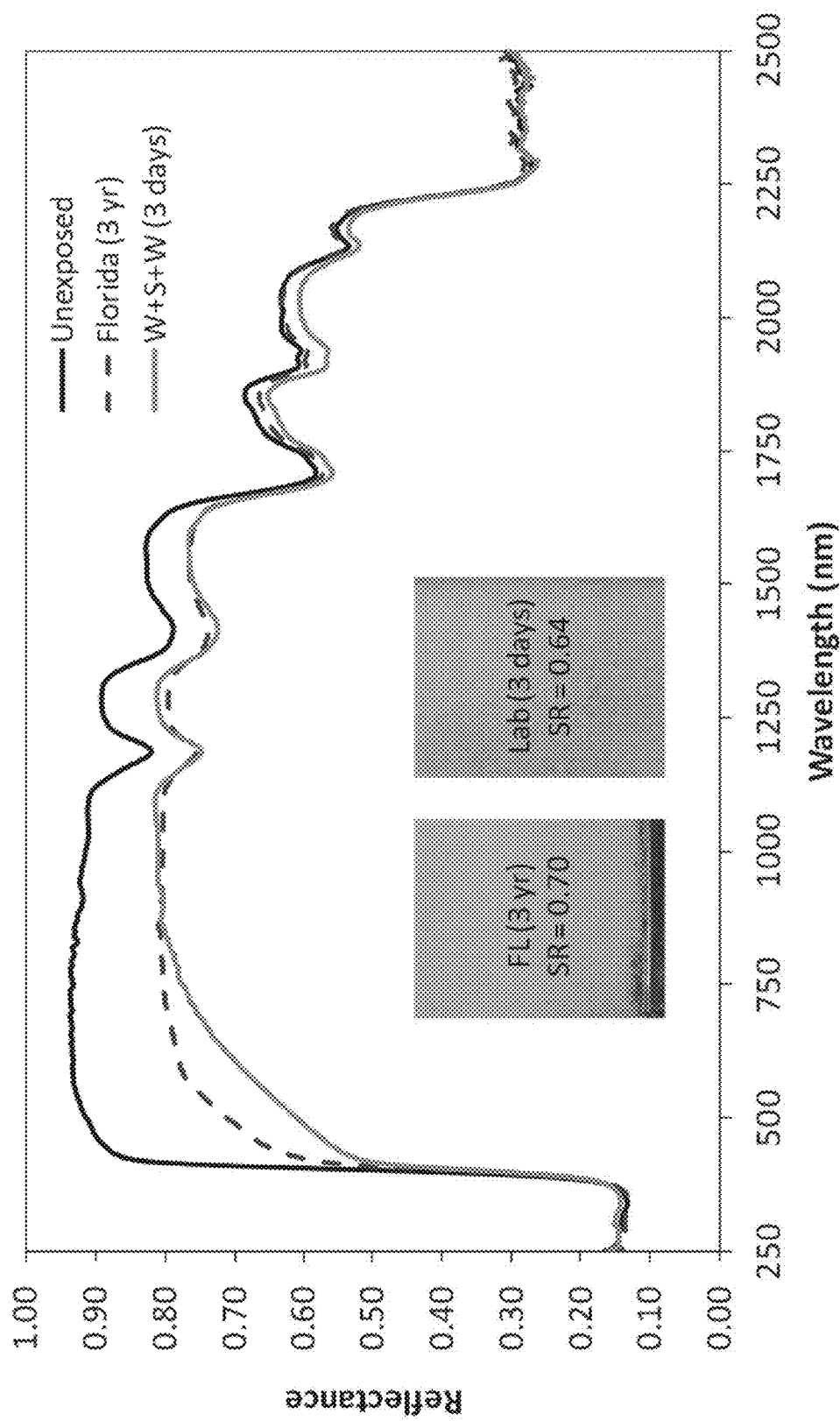
Figure 18:
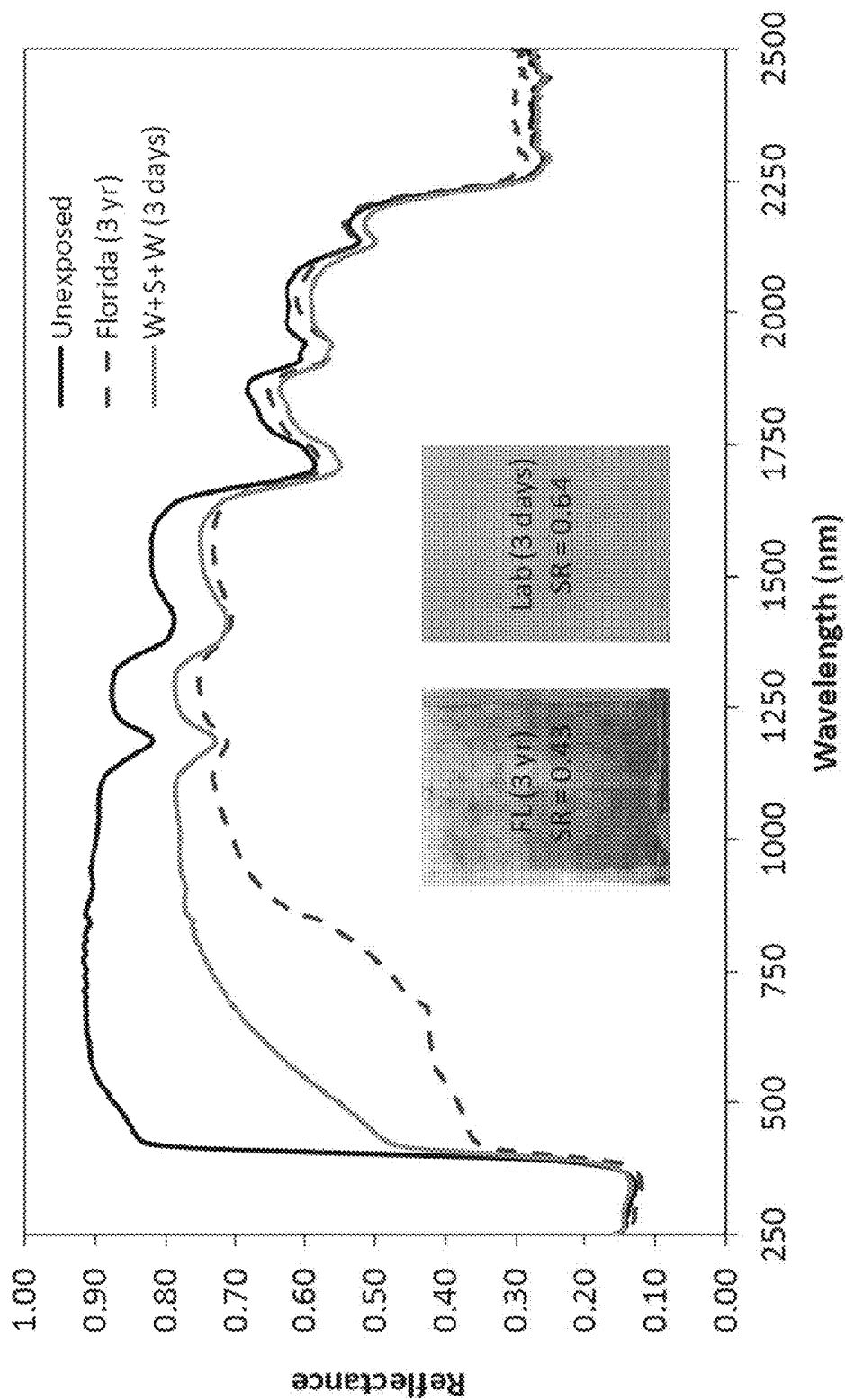

Coupons of one sample (a white field-applied coating) that had been naturally exposed for three years in the three different climates were compared to coupons of the same sample laboratory-aged for three days using the simulated aging process (weathering+soiling+weathering) of the embodiments disclosed herein using the mixtures shown in FIG. 14. FIGS. 15-18 compare the solar spectral reflectance obtained in the laboratory with those obtained for the same materials unexposed (clean) and naturally aged for 3-years at each of the three U.S. exposure locations. More specifically, FIG. 15 shows the reflectance spectra of unexposed, 3-year aged (Arizona), and laboratory aged white coating using the simulated aging process (soiling mixture specific to Arizona). FIG. 16 shows the reflectance spectra of unexposed, 3-year aged (Ohio), and laboratory aged white coating using the simulated aging process (soiling mixture specific to Ohio). FIG. 17 shows the reflectance spectra of unexposed, 3-year aged (Florida), and laboratory aged white coating using the simulated aging process (soiling mixture specific to Florida). FIG. 18 shows the reflectance spectra of unexposed, 3-year aged (Florida), and laboratory exposed white coating (a second coupon) using the simulated aging process (soiling mixture specific to Florida).

The results of the simulated aging methods of the embodiments disclosed herein show excellent matches to samples naturally exposed in Arizona and Ohio. Not only did the solar reflectance obtained in the laboratory (in three days) match well with that of 3-year aged samples, but the change in the spectral reflectance across the solar spectrum was also close to that observed for naturally aged samples.

The reflectance spectra of the lab-aged (simulated) coupons of FIG. 18 differed partially from those of the coupons exposed in Florida, notably in the visible spectrum (i.e., 400 nm to 700 nm). It is believed that the reason the lab-soiled samples did not exhibit the same loss of reflectance in the UV-visible region as samples exposed in a Florida (hot and humid climate) is that microorganisms, such as algae, grow on samples in this hot and humid climate. Despite this mismatch with the data from the 3 year exposure in Florida for this heavy soiled sample, the developed methodology remains valuable for prototyping of new roofing materials and evaluation of their overall resistance to soiling by components of atmospheric particulate matter. Efforts are underway to integrate additional soiling surrogates for microbial growth, an important factor to be considered in the development of future soiling processes for this hot and humid climate condition.

CONCLUSION

The embodiments disclosed herein have been described in considerable detail to provide those skilled in the art with information relevant to apply the novel principles and to construct and use such specialized components as are required. However, it is to be understood that the embodiments can be carried out by different equipment, materials, and devices, and that various modifications, both as to the equipment and operating procedures, can be accomplished without departing from the scope of the embodiments.

We claim:

1. A method of simulating the aging of a sample of a roofing material, the method comprising:
   (a) weathering the sample positioned in a chamber in a first exposure of the sample to ultraviolet light, water vapor, and elevated temperatures, the first exposure including heating the sample to about 55° C. to 65° C. for about 7 hours to 9 hours, cooling the sample from about 55° C. to 65° C. to about 45° C. to 55° C., and exposing the sample to water vapor at about 45° C. to 55° C. for about 3 hours to 5 hours;
   (b) after operation (a), depositing a soiling mixture on the sample, the soiling mixture comprising salt, soot, mineral dust, and humic acid, the mineral dust comprising iron oxide, montmorillonite, and bentonite; and
   (c) after operation (b), weathering the sample positioned in the chamber in a second exposure of the sample to ultraviolet light, water vapor, and elevated temperatures, the second exposure including heating the sample to about 55° C. to 65° C. for about 7 hours to 9 hours, cooling the sample from about 55° C. to 65° C. to about 45° C. to 55° C., and exposing the sample to water vapor at about 45° C. to 55° C. for about 3 hours to 5 hours, operations (a), (b), and (c) aging the sample at an accelerated rate compared to aging of the sample in an outdoor environment.

2. The method of claim 1, wherein the ultraviolet light in the first exposure is Ultraviolet A light.

3. The method of claim 1, wherein the first exposure is performed twice in a period of about 24 hours.

4. The method of claim 1, wherein the first exposure and the second exposure include:
   heating the sample to about 60° C. for about 8 hours;
   cooling the sample from about 60° C. to about 50° C.; and
   exposing the sample to water vapor at about 50° C. for about 4 hours.

5. The method of claim 1, wherein the ultraviolet light in the second exposure is Ultraviolet A light.

6. The method of claim 1, wherein the second exposure is performed twice in a period of about 24 hours.

7. The method of claim 1, wherein the soiling mixture includes the salt at about 7% to 31% by weight, the soot at about 1% to 8% by weight, the mineral dust at about 16% to 79% by weight, and the humic acid at about 0% to 69% by weight.

8. The method of claim 1, wherein the soiling mixture includes the salt at about 18% to 27% by weight, the soot at about 4% to 12% by weight, the mineral dust at about 28% to 66% by weight, and the humic acid at about 8% to 36% by weight.

9. The method of claim 1, wherein each component in the soiling mixture is suspended in an aqueous medium when depositing the soiling mixture on the sample, the method further comprising:
   drying the sample with a near infrared heat lamp after depositing the soiling mixture on the sample.

10. The method of claim 1, wherein operation (b) includes depositing the soiling mixture to substantially uniformly cover a surface of the sample.

11. The method of claim 1, wherein after operation (b) the sample is substantially uniformly covered with agglomerations of the soiling mixture, and wherein the agglomerations have a dimension of about 1.5 millimeters to 3 millimeters.

12. The method of claim 1, further comprising:
    prior operation (b), preparing the soiling mixture by mixing amounts of the salt, the soot, the mineral dust, and the humic acid in water.

13. The method of claim 1, wherein operation (b) is performed by spraying the soiling mixture on the sample using a nozzle.

14. The method of claim 1, further comprising:
    (d) after operation (c), measuring a solar reflectance spectra or a thermal emittance of the sample.

15. A method of simulating the aging of a sample of a roofing material, the method comprising:
    (a) weathering the sample positioned in a chamber in a first exposure of the sample to ultraviolet light generated by an ultraviolet lamp, water vapor, and elevated temperatures generated by a heating element;
    (b) after operation (a), depositing a specified soiling mixture on the sample by spraying the specified soiling mixture on the sample using a nozzle, the specified soiling mixture comprising salt, soot, mineral dust, and humic acid in an aqueous suspension, the mineral dust comprising iron oxide, montmorillonite, and bentonite;
    (c) after operation (b), drying the sample with a near infrared heat lamp; and
    (d) after operation (c), weathering the sample positioned in the chamber in a second exposure of the sample to ultraviolet light generated by the ultraviolet lamp, water vapor, and elevated temperatures generated by the heating elements, operations (a), (b), (c), and (d) aging the sample at an accelerated rate compared to aging of the sample in an outdoor environment.

16. The method of claim 15, wherein the first exposure and the second exposure include:
    heating the sample to about 55° C. to 65° C. for about 7 hours to 9 hours;
    cooling the sample from about 55° C. to 65° C. to about 45° C. to 55° C.; and
    exposing the sample to water vapor at about 45° C. to 55° C. for about 3 hours to 5 hours.

17. The method of claim 15, wherein the first exposure and the second exposure include:
    heating the sample to about 60° C. for about 8 hours;
    cooling the sample from about 60° C. to about 50° C.; and
    exposing the sample to water vapor at about 50° C. for about 4 hours.

18. A method of simulating the aging of a sample of a roofing material, the method comprising:
    (a) mixing specified amounts of salt, soot, mineral dust, and humic acid in an aqueous solution to prepare a specified soiling mixture, the mineral dust comprising iron oxide, montmorillonite, and bentonite;
    (b) weathering the sample positioned in a chamber in a first exposure of the sample to ultraviolet light generated by an ultraviolet lamp, water vapor, and elevated temperatures generated by a heating element;
    (c) after operation (b), depositing the specified soiling mixture on the sample by spraying the specified soiling mixture on the sample using a nozzle; and
    (d) after operation (c), weathering the sample positioned in the chamber in a second exposure of the sample to ultraviolet light generated by the ultraviolet lamp, water vapor, and elevated temperatures generated by the heating elements, operations (b), (c), and (d) aging the sample at an accelerated rate compared to aging of the sample in an outdoor environment.

19. The method of claim 18, wherein the first exposure and the second exposure include:

heating the sample to about 55° C. to 65° C. for about 7 hours to 9 hours;

cooling the sample from about 55° C. to 65° C. to about 45° C. to 55° C.; and exposing the sample to water vapor at about 45° C. to 55° C. for about 3 hours to 5 hours.

20. The method of claim 18, wherein the first exposure and the second exposure include:

heating the sample to about 60° C. for about 8 hours;

cooling the sample from about 60° C. to about 50° C.; and exposing the sample to water vapor at about 50° C. for about 4 hours.

\* \* \* \* \*